(12) United States Patent
Li et al.

(10) Patent No.: US 6,654,728 B1
(45) Date of Patent: Nov. 25, 2003

(54) FUZZY LOGIC BASED CLASSIFICATION (FLBC) METHOD FOR AUTOMATED IDENTIFICATION OF NODULES IN RADIOLOGICAL IMAGES

(75) Inventors: Ruiping Li, Rockville, MD (US); Hwa-Young Michael Yeh, Potomac, MD (US); Yuan-Ming Fleming Lure, Potomac, MD (US); Xin-Wei Xu, Gaithersburg, MD (US); Jyh-Shyan Lin, North Potomac, MD (US)

(73) Assignee: Deus Technologies, LLC, Rockville, MD (US)

( * ) Notice: Subject to any disclaimer, the term of this patent is extended or adjusted under 35 U.S.C. 154(b) by 490 days.

(21) Appl. No.: 09/625,418

(22) Filed: Jul. 25, 2000

(51) Int. Cl.[7] .............................................. G06F 15/18
(52) U.S. Cl. ......................................................... 706/2
(58) Field of Search ............................................ 706/2

(56) References Cited

U.S. PATENT DOCUMENTS 5,014,197 A * 5/1991 Wolf ............................ 710/38
5,371,853 A * 12/1994 Ko et al. .................. 704/200.1
6,138,045 A * 10/2000 Kupinski et al. ............ 600/425
6,353,674 B1 * 3/2002 Dewaele ..................... 382/132

OTHER PUBLICATIONS

Burges etal, " Shortest Path Segmentation: A Method for Training a Neural Network to Recognize Character Strings", IEEE IJCNN, Jun. 1992.*

Noburu Funakubo, " Feature Extraction of Color Texture Using Neural Networks for Region Segmentation", IEEE IECON, Sep. 1994.*

* cited by examiner

Primary Examiner—George B. Davis
(74) Attorney, Agent, or Firm—Venable LLP; Robert Kinberg; Jeffrey W. Gluck

(57) ABSTRACT

A fuzzy logic based classification (FLBC) method for the automated discrimination of objects and the automated identification of nodules based on their features, a computer programmed to implement the method, and a storage medium which stores a program for implementing the method, wherein nodule (or, object) features are first normalized and then automatically selected. Based on the selected features, suspect nodules (or, objects) are pre-grouped and then subjected to the corresponding trained linear classifier to remove those false positive nodules or abnormal objects that are linearly separable. Finally, the remaining suspect nodules or objects are further subjected to a trained fuzzy classifier for removing those false positive nodules or abnormal objects that are not linearly separable.

37 Claims, 12 Drawing Sheets

FUZZY LOGIC BASED CLASSIFICATION (FLBC) METHOD FOR AUTOMATED IDENTIFICATION OF NODULES IN RADIOLOGICAL IMAGES

BACKGROUND OF THE INVENTION

1. Field of the Invention

The present invention relates to methods and systems for the digital processing of radiological images, and it more specifically relates to an automated method and system for the re-screening and detection of abnormalities, such as lung nodules in radiological chest images, using multi-resolution processing, digital image processing, fuzzy logic and artificial neural networks.

2. Background Art

Lung cancer is the leading type of cancer in both men and women worldwide. Early detection and treatment of localized lung cancer at a potentially curable stage can significantly increase the patients' survival rate. Studies have shown that approximately 68% of retrospectively detected lung cancers were detected by one reader and approximately 82% were detected with an additional reader as a "second-reader". A long-term lung cancer screening program conducted at the Mayo Clinic found that 90% of peripheral lung cancers were visible in small sizes in retrospect, in earlier radiographs.

Among the common detection techniques, such as chest X-ray, analysis of the types of cells in sputum specimens, and fiber optic examination of bronchial passages, chest radiography remains the most effective and widely used method. Although skilled pulmonary radiologists can achieve a high degree of accuracy in diagnosis, problems remain in the detection of the lung nodules in chest radiography due to errors that cannot be corrected by current methods of training even with a high level of clinical skill and experience.

An analysis of the human error in diagnosis of lung cancer revealed that about 30% of the misses were due to search errors, about 25% of the misses were due to recognition errors, and about 45% of the misses were due to decision-making errors. Reference is made to Kundel, H. L., et al., "Visual Scanning, Pattern Recognition and Decision-Making in Pulmonary Nodule Detection", Investigative Radiology, May–June 1978, pages 175–181, and Kundel, H. L., et al., "Visual Dwell Indicates Locations of False-Positive and False-Negative Decisions", Investigative Radiology, June 1989, Vol. 24, pages. 472–478, which are incorporated herein by reference. The analysis suggested that the miss rates for the detection of small lung nodules could be reduced by about 55% with a computerized method. According to the article by Stitik, F. P., "Radiographic Screening in the Early Detection of Lung Cancer", Radiologic Clinics of North America, Vol. XVI, No. 3, December 1978, pages 347–366, which is incorporated herein by reference, many of the missed lesions would be classified as T1M0 lesions, the stage of non-small cell lung cancer that Mountain, C. F. "Value of the New TNM Staging System for Lung Cancer", 5th World Conference in Lung Cancer Chest, 1989 Vol. 96/1, pages 47–49, which is incorporated herein by reference, indicates has the best prognosis (42%, 5 year survival). It is this stage of lung cancer, with lesions less than 1.5 cm in diameter, and located outside the hilum region that need to be detected by a radiologist in order to improve survival rates.

Computerized techniques, such as computer aided diagnosis (CAD), have been introduced to assist in the diagnosis of lung nodules during the stage of non-small cell lung cancer. The CAD technique requires the computer system to function as a second physician to double check all the films that a primary or first physician has examined. Reduction of false positive detection is the primary objective of the CAD technique in order to improve detection accuracy.

Several CAD techniques using digital image processing and artificial neural networks have been described in numerous publications, exemplary of which are the following, which are incorporated herein by reference:

U.S. Pat. No. 4,907,156 to Doi et al. describes a method for detecting and displaying abnormal anatomic regions existing in a digital X-ray image. A single projection digital X-ray image is processed to obtain signal-enhanced image data with a maximum signal-to-noise ratio (SNR) and is also processed to obtain signal-suppressed image data with a suppressed SNR. Then, difference image data are formed by subtraction of the signal-suppressed image data from the signal-enhanced image data to remove low-frequency structured anatomic background, which is basically the same in both the signal-suppressed and signal-enhanced image data. Once the structured background is removed, feature extraction is performed. For the detection of lung nodules, pixel thresholding is performed, followed by circularity and/or size testing of contiguous pixels surviving thresholding. Threshold levels are varied, and the effect of varying the threshold on circularity and size is used to detect nodules. For the detection of mammographic microcalcifications, pixel thresholding and contiguous pixel area thresholding are performed. Clusters of suspected abnormalities are then detected. However, the algorithm described in the Doi et al. patent seems to reduce false positive rates at the expense of missing several true nodules. This prior art is limited in detection of nodules with size larger than its pre-selected size –1.5 cm. This prior art will also reduce the sensitivity by selecting fixed CDF thresholds (e.g., 97%, 94%, 91%, etc.) since some true nodules will be eliminated during this thresholding process. The algorithm described in the Doi et al. patent utilizes a single classifier (a decision tree classifier) which possesses inherent performance. A decision tree classifier performs classification by eliminating true positives in a sequential way; hence, it is easy to eliminate potential nodules in the first decision node even if the rest of the decision criteria are satisfied. Another important drawback to this prior art is that the physician has to examine every film with both true and false positives identified by the CAD system, so the time spent on the diagnosis increases dramatically.

U.S. Pat. No. 5,463,548 to Asada et al. describes a system for computer-aided differential diagnosis of diseases, and in particular, computer-aided differential diagnosis using neural networks. A first design of the neural network distinguishes between a plurality of interstitial lung diseases on the basis of inputted clinical parameters and radiographic information. A second design distinguishes between malignant and benign mammographic cases based upon similar inputted clinical and radiographic information. The neural networks were first trained using a hypothetical database made up of hypothetical cases for each of the interstitial lung diseases and for malignant and benign cases. The performance of the neural network was evaluated using receiver operating characteristics (ROC) analysis. The decision performance of the neural network was compared to experienced radiologists and achieved a high performance comparable to that of the experienced radiologists. However, Asada's method seems limited to the detection of lung diseases but not lung cancer, which presents different symptoms.

Y. S. P. Chiou, Y. M. F. Lure, and P. A. Ligomenides, "Neural Network Image Analysis and Classification in Hybrid Lung Nodule Detection (HLND) System", Neural Networks for Processing III Proceedings of the 1993 IEEE-SP Workshop, pp. 517–526. The Chiou et al. article describes a Hybrid Lung Nodule Detection (HLND) system based on artificial neural network architectures, which is developed for improving diagnostic accuracy and speed of lung cancerous pulmonary radiology. The configuration of the HLND system includes the following processing phases: (1) pre-processing to enhance the figure-background contrast; (2) quick selection of nodule suspects based upon the most pertinent feature of nodules; and (3) complete feature space determination and neural classification of nodules. The Chiou et al. article seems to be based on U.S. Pat. No. 4,907,156 to Doi et al., but adds a neural network approach. The Chiou et al. system includes similar shortcomings to those in the Doi et al. system described in U.S. Pat. No. 4,907,156.

S. C. Lo, J. S. Lin, M. T. Freedman, and S. K. Mun, "Computer-Assisted Diagnosis of Lung Nodule Detection Using Artificial Convolution Neural Network", Proceeding of SPIE Medical Imaging VI, Vol. 1898, 1993, describes a nodule detection method using a convolutional neural network consisting of a two-dimensional connection trained with a back propagation learning algorithm, in addition to thresholding and circularity calculation, morphological operation, and a 2-D sphere profile matching technique. The use of a very complicated neural network architecture, which was originally developed for optical character recognition in binary images, the lengthy training time, and the lack of focus on the reduction of false positives, renders the published nodule detection methods impractical. This prior art also possesses similar drawbacks to the Doi et al. system described in U.S. Pat. No. 4,907,156.

S. C. Lo, S. L. Lou, S. Lin, M. T. Freedman, and S. K. Mun, "Artificial convolution neural network techniques for lung nodule detection", IEEE Trans. Med. Imag. Vol 14, pp 711–718, 1995, describes a nodule detection method using a convolutional neural network consisting of a two-dimensional connection trained with a back propagation learning algorithm, in addition to thresholding and circularity calculation, morphological operation, and a 2-D sphere profile matching technique. This prior art also possesses similar drawbacks to the Doi et al. system and the system described in Lo, et al., 1993.

J.-S. Lin, P. Ligomenides, S.-C. B. Lo, M. T. Freedman, S. K. Mun, "A Hybrid Neural-Digital Computer Aided Diagnosis System for Lung Nodule Detection on Digitized Chest Radiographs", Proc. 1994 IEEE Seventh Symp. on Computer Based Medical Systems, pp. 207–212, describes a system for the detection and classification of cancerous lung nodules utilizing image processing and neural network. However, the system described in this article suffers from similar shortcomings as the system described in the Lo et al. article.

M. L. Giger, "Computerized Scheme for the Detection of Pulmonary Nodules", Image Processing VI, IEEE Engineering in Medicine & Biology Society, 11$^{th}$ Annual International Conference (1989), describes a computerized method to detect locations of lung nodules in digital chest images. The method is based on a difference-image approach and various feature-extraction techniques, including a growth test, a slope test, and a profile test. The aim of the detection scheme is to direct the radiologist's attention to locations in an image that may contain a pulmonary nodule, in order to improve the detection performance of the radiologist. However, the system described in this article suffers from similar shortcomings to the system described in Doi et al.

SUMMARY OF THE INVENTION

One object of this invention is to provide a novel classification method, based on fuzzy logic, soft optimization, and feature selection techniques, for automated nodule identification in computer-aided diagnosis. The invention further enables the identification of lung nodules in which classification is feature-based. The invention also can be used for other classification problems and detection of diseases, including but not limited to microcalcification clusters, masses and tumors.

Additionally, the invention may be embodied as a computer programmed to carry out the inventive method, as a storage medium storing a program for implementing the inventive method, and as a system for implementing the method.

The automated classification method of the present invention uses several advanced techniques, such as fuzzy logic, optimized linear partition, and feature-weighted detector (FWD) network to eliminate false positive nodules, thus greatly improving performance. Once image data is acquired from a radiological chest image, the data is subjected to a multi-phase digital image processing technique to initially identify several suspect regions. First, during the image enhancement phase, object-to-background contrast of the data is enhanced using multi-resolution matching techniques. Next, during the quick selection phase, the data is subjected to sphericity testing, involving examination of circularity parameters of each grown region in a sliced (thresholding) image obtained from a series of pixel threshold values, and segmentation of suspect object blocks to preliminarily select nodule candidates. The pixel threshold values are derived based on the desired suspect nodule area (SNA) number and size, signal-to-noise ratio (SNR) of the image, and CDF of the image in order to have maximal sensitivity. In the feature extraction phase, plausible features of nodules are further extracted from the corresponding region. In the classification phase, the objective of identifying a true positive nodule among suspect nodule candidates is achieved according to the present invention by using following steps: a) normalizing feature values; b) selecting meaningful features from among the normalized features; c) pre-grouping nodules in several sub-groups according to their selected (meaningful) features; d) subjecting the objects to trained linear classifiers corresponding to their sub-groups; and e) using a trained fuzzy classifier to further discriminate true positive nodules from false positive nodules. In the final phase, the decision making phase, the suspect nodules are analyzed using prevalence rate, risk factor, and system performance to determine portion of the films for further reviewing. The use of these multiple resolution techniques, multiple classifiers, and presentation of a portion of highly suspect films for a physician's final diagnosis eliminates a high number of false positives experienced using prior art techniques and increases the detection accuracy.

According to the method of the present invention, step a) includes employing vertical offset normalization to remove insignificant yet strong characteristics in data, thereby enhancing weak yet significant information for identifying true positives.

According to the method of this invention, step b) includes developing a feature-weighted detector (FWD) network based on a semi-supervised learning scheme.

Preferably, the FWD is a bidirectional connection neural network in which there are two types of connections. Memory connection trained by an unsupervised learning law represents summarization of learning results. Weight connection trained by a supervised learning law represents degree of importance of each feature. Input data presented to the input layer of the FWD are image features including effective diameter, degree of circularity, degree of irregularity, slope of the effective diameter, slope of degree of circularity, slope of degree of irregularity, average gradient, standard deviation of gradient orientation, contrast and net contrast. Each image feature applied to the input layer is normalized by using step a) to evaluate the value without effects of scale. After running, FWD gives a weight for each feature. The more meaningful a feature is, the larger its weight is; if the weight approaches zero, then the corresponding feature is meaningless.

Step c) includes using a gaussian clustering method (GCM) to pre-group nodules. Preferably, this pre-grouping method is based on a self-organizing algorithm by which sub-structures in data would be found without prior knowledge. Therefore, the method of step c) of the invention enables reducing false positives while maintaining recognition rate.

In suspect nodules (SNs) selected by the quick selection phase, the number of true positive nodules is much less than that of false positive nodules. Further, the majority of false positive nodules do not overlap, in terms of feature matching (i.e., "feature-wise"), with true positive nodules. This brings about the difficulty of identifying the true positive nodules. In the present invention, therefore, two types of classifiers are introduced. Step d) refers to the first level classification that focuses on reducing those false positive nodules that do not overlap feature-wise with true positive nodules. Step e) performs the second level classification algorithm that focuses on reducing the rest of the false positive nodules that overlap feature-wise with true positive nodules. According to the method of the invention, the first level classifier comprises an optimized linear partition (OLP) technique. The problem of OLP is defined by an unconstrained quadratic objective function. After OLP, the optimal solution to reduction of false positive nodules would be found. That is to say, the method can reduce the number of false positives without loss of true positives. Preferably, OLP also can be used for each of a number of sub-groups of suspect nodules, and the processing time is considered almost negligible compared to that of using traditional neural networks.

In step e), the second level classifier is a fuzzy structure classifier (FSC) based on a semi-supervised learning scheme. Preferably, a FSC consists of a set of rules in IF-THEN form. The premise part of each rule expresses fuzzy structures in data. The consequence part of each rule expresses a clear relationship between inputs and output. Therefore, each rule can be described in natural language.

DEFINITIONS

A "computer" refers to any apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; and a hybrid combination of a computer and an interactive television. A computer also refers to two or more computers connected together via a network for transmitting or receiving information between the computers. An example of such a computer includes a distributed computer system for processing information via computers linked by a network.

A "computer-readable medium" refers to any storage device used for storing data accessible by a computer. Examples of a computer-readable medium include: a magnetic hard disk; a floppy disk; an optical disk, such as a CD-ROM and a DVD; a magnetic tape; a memory chip; and a carrier wave used to carry computer-readable electronic data, such as those used in transmitting and receiving e-mail or in accessing a network.

"Software" refers to prescribed rules to operate a computer. Examples of software include: software; code segments; instructions; computer programs; and programmed logic.

A "computer system" refers to a system having a computer, where the computer includes a computer-readable medium embodying software to operate the computer.

An "information storage device" refers to an article of manufacture used to store information. An information storage device can have different forms, for example, paper form and electronic form. In paper form, the information storage device includes paper printed with the information. In electronic form, the information storage device includes a computer-readable medium storing the information as software, for example, as data.

BRIEF DESCRIPTION OF THE DRAWINGS

The features of the present invention and the manner of attaining them will become apparent, and the invention itself will be understood by reference to the following description and the accompanying drawings, wherein.

DETAILED DESCRIPTION OF THE PREFERRED EMBODIMENTS

Figure 1:
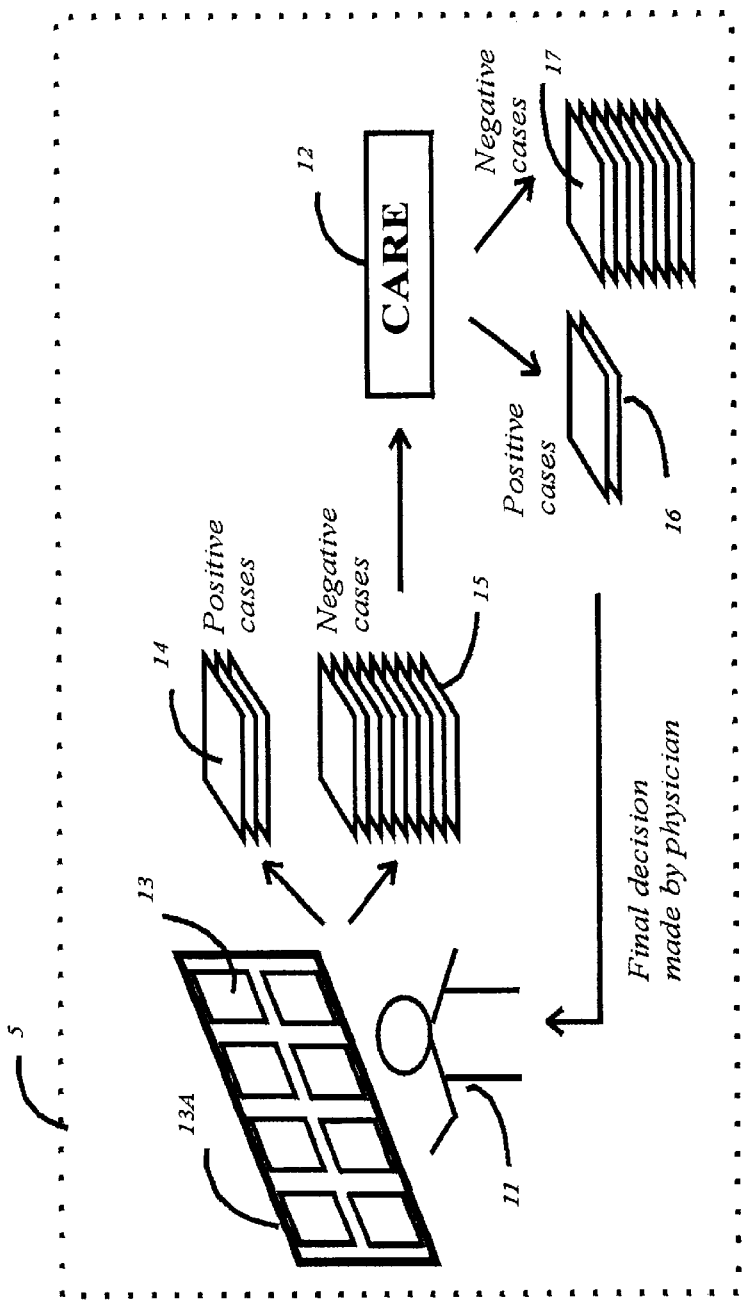
FIG. 1 is a diagram of a process for re-screening lung nodules for the detection of lung cancer.

FIG. 1 illustrates the inventive diagnostic technique, which improves the detection of suspect nodules. The patients' chest X-ray films 13 are first mounted in a light box 13A in a radiological setting. A physician examines the films 13 to determine the existence of suspect lung nodules in the films 13. Films determined by the physician to contain suspect nodules are set aside as positive films 14 for further radiological diagnosis. Negative films 15 determined by the physician to contain no suspect nodules are sent to a computer aided re-screen (CARE) system 12 of the present invention for further detection.

The CARE system 12 is a computer-based system involving multiple stages of processing. Two types of cases are determined by the CARE system 12: positive cases (or "review" cases) 16 and negative cases (or "non-review" cases) 17. The positive cases 16 are sent back to the physician for final decision based on the chest X-ray films.

The method and procedure of present invention can be utilized in two modes: (1) the batch mode, where radiological staff collects a set of negative films to process in CARE 12; and (2) the interactive mode, where physicians run the negative film through CARE 12 immediately after the physician makes an initial diagnosis.

Figure 2:
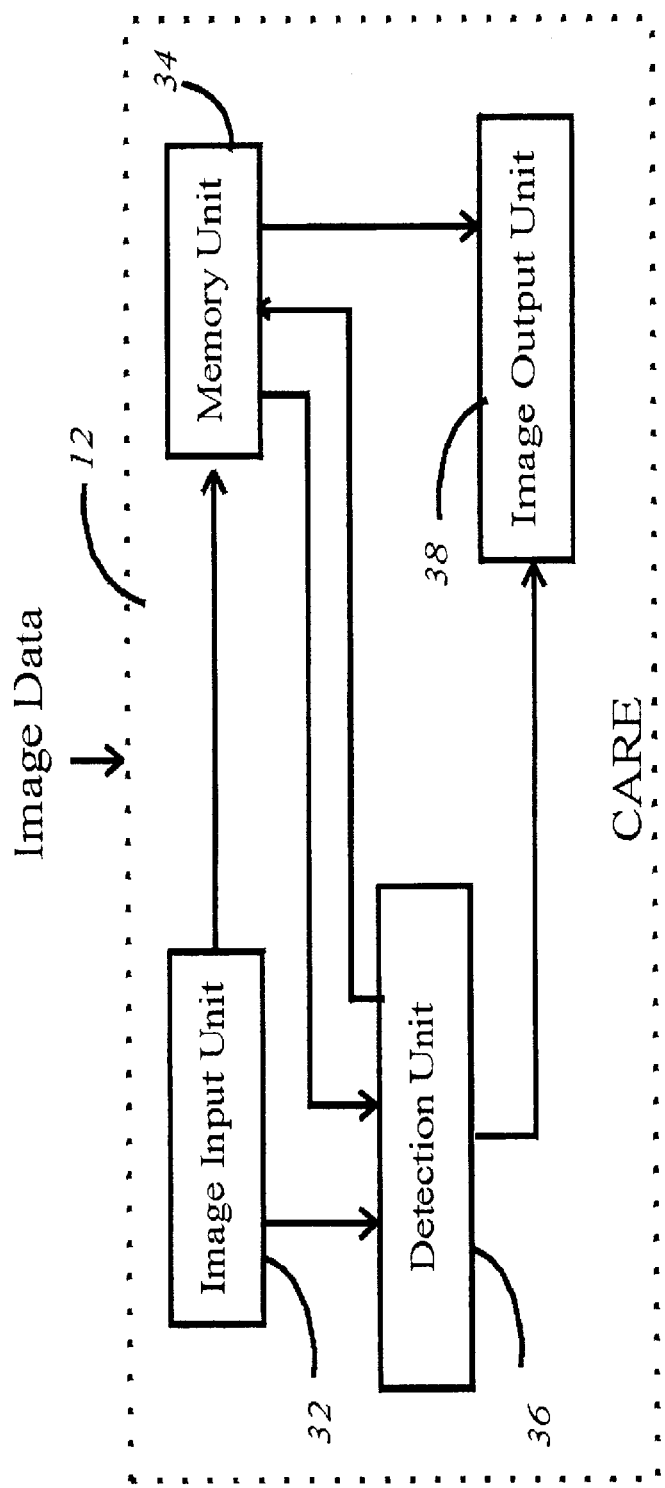
FIG. 2 is a block diagram of a process used by a re-screening unit forming part of the computer aided re-screening (CARE) unit of FIG. 1.

FIG. 2 illustrates a CARE system 12 for digital processing of radiological images according to the present invention. Although the system 12 and method of operation will be described herein in relation to the automated detection and re-screening of lung nodules in radiological chest images using digital image processing, multi-resolution processing, and artificial neural networks, it should be understood that the system 12 and its method of operation may be used in numerous other digital image processing applications.

Using the system 12, image data of an anatomic region of interest, such as a chest (not shown), is entered into an image input unit 32. The input data may be provided for example by a video camera, computer radiograph (CR) system, direct digital radiography (DDR) system, picture archive and communication (PACS) system, or a film digitizer. The data in the image input unit 32 is stored for later retrieval and use in a memory unit 34, or sent to an detection unit 36. Any suitable memory unit device 34, such as magnetic tape, computer disk, optical laser storage, etc., can be utilized. The detection unit 36 applies the detection method (which includes the re-screening method to be discussed later) of the present invention to the input image to detect lung nodules within the image. As will be described later in greater detail, the detection unit 36 includes multiple phases that generally correspond to the several main steps of the detection method of the present invention. Subsequently, the image is sent to the memory unit 34 for storage and/or to an image output unit 38, such as a monitor, a printer, a plotter, a chart recorder, or the like.

Figure 3:
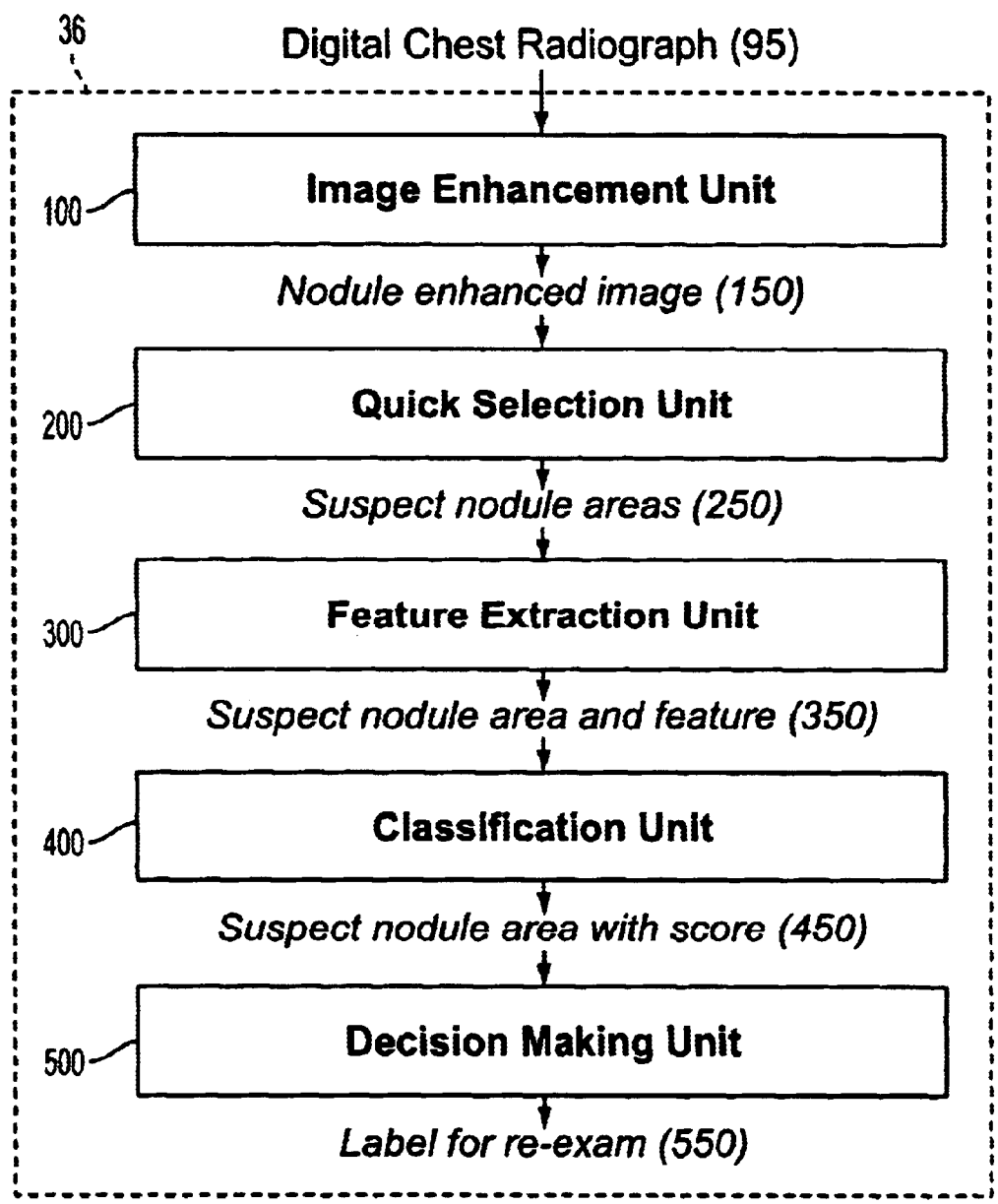
FIG. 3 is a block diagram of a detection unit forming part of the system of FIG. 2.

With reference to FIG. 3, the detection unit 36 generally includes multiple phases or stages. In the first phase, an image enhancement unit 100 performs multi-resolution decomposition and matching in order to enhance the object-to-background contrast in an input digital radiograph 95; thus producing a nodule-enhanced image (150).

In the second phase, a quick selection unit 200 performs sphericity testing of smaller regions in a series of sliced images, and several suspect nodule (SN) areas are then segmented and selected, in order to identify suspect areas (for example 32×32 pixels) 250, which may include abnormalities (i.e., nodules).

During the third phase, a feature extraction unit 300 generates plausible features for each of suspect nodules (SNs) selected by the above quick selection unit to classify SNs (350). Basically, plausible features considered include: effective diameter, degree of circularity, degree of irregularity, slope of the effective diameter, slope of degree of circularity, slope of degree of irregularity, average gradient, standard deviation of gradient orientation, contrast and net contrast.

The fourth phase is a classification unit 400 in which five sub-phases are included. These are feature value normalization, feature selection, SN pre-grouping, optimized linear partition (OLP) phase and fuzzy structure classifier (FSC) phase. The final selected SNs are associated with a classification score (450).

During the fifth phase, a decision making unit 500 employs occurrence evaluation, fraction determination, classification threshold determination, and reviewing thresholding to select a small portion of positive films to be labeled for re-exam (550), for further diagnostic review.

Having briefly described the five phases of the detection unit 36 a more detailed description of the inventive fourth phase will follow.

The classification unit 400 of FIG. 3 will be described with reference to FIG. 4. The classification unit 400 processes the suspect nodule area with feature 350 in the feature value normalization part 4100, feature selection part 4200, suspect nodule pre-grouping part 4300, optimized linear partition part 4400 and fuzzy structure classifier part 4500 to reduce false positive nodules.

Figure 5:
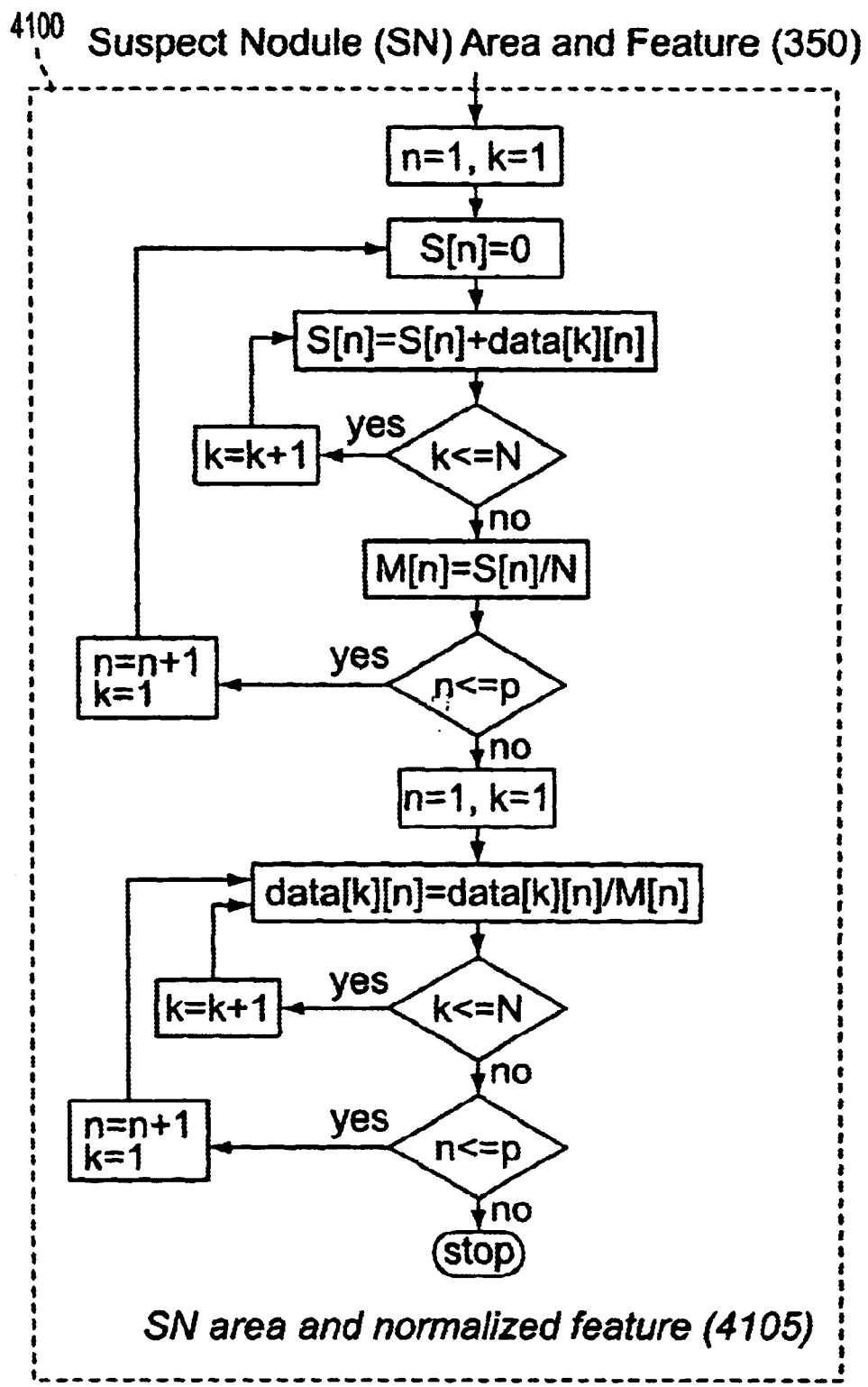
FIG. 5 is a flow chart illustrating steps in the feature normalization part of the classification unit of FIG. 4.

The feature value normalization part 4100 performs a vertical offset normalization algorithm as shown in FIG. 5 to remove insignificant yet strong characteristics in data. In the algorithm, N is the total number of patterns (i.e., suspect nodules), and p is the total number of features. In many cases, significant information is contained in small variations added to a large offset. The offset should be removed if it is known to be irrelevant, as it may inhibit training and classification. Through the normalization process, the effects of having different feature scales are avoided, thus permitting the selection of meaningful features among the plausible feature set (4105).

Figure 6:
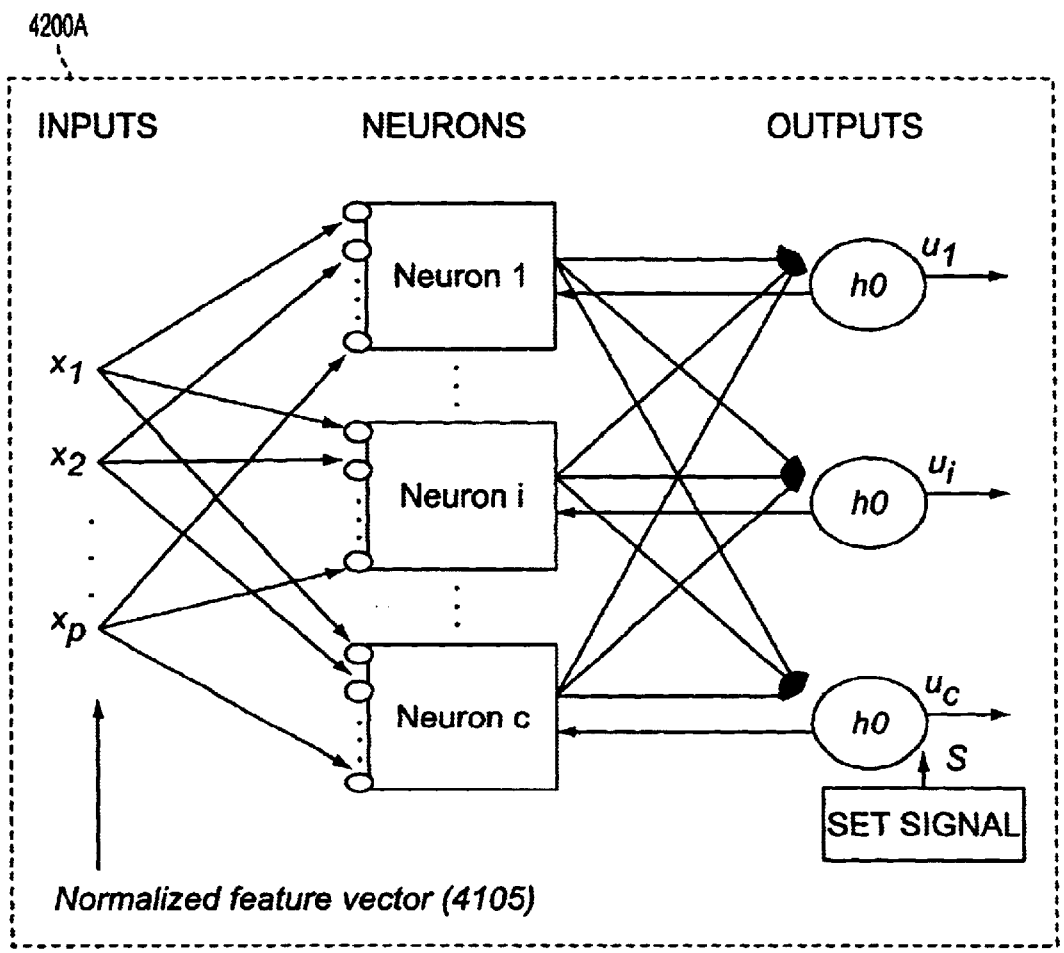
FIG. 6 is a schematic diagram of the FWD network in the feature selection part of the classification unit of FIG. 4.
Figure 7:
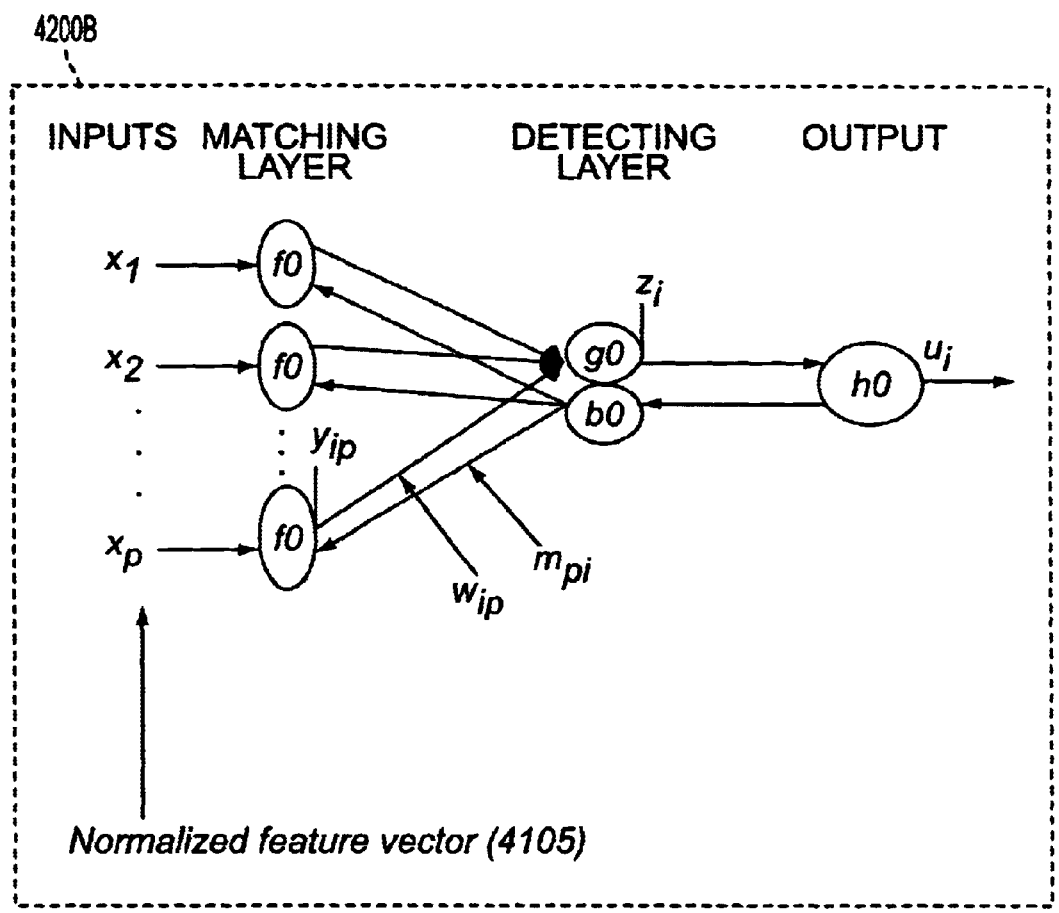
FIG. 7 illustrates the structure of neuron i and signal propagation in the FWD network of FIG. 6.

The feature selection part 4200 employs a fuzzy neural network to select meaningful features (350) among the plausible feature set generated by the feature extraction unit. The developed fuzzy neural network is called a feature-weighted detector (FWD) network and is shown in FIG. 6 and FIG. 7. The FWD consists of input (I), matching (M), detecting (D) and output (O) layers (FIG. 7). This will be described in further detail below.

Each M node can receive inputs from 2 sources: the left-right input; and right-left input from a node of D via a D-M adaptive connection. f( ) is a comparative function, and the output is the difference of two input values. In the detecting layer, there are two types of nodes: forward and backward nodes. Each forward-node receives p inputs from p nodes of M via pathways with weight connections $\{w_{ij}\}$. g( ) represents a Gaussian function. Each backward-node receives input from a node of O via a backward-pathway with one connection fixed. b( ) is a linear function. The function of the output layer nodes is to normalize output values of all nodes. Each O node receives c+1 inputs. One of them is called a set signal. The other c are from D via c pathways with one connection fixed. The set signal occurs before input is presented to the input layer. The role of the set signal is to provide an equal opportunity to match the input for each of the nodes of M. Therefore, all input-output functions are written as $$y_{ij}=(x_{kj}-m_{ji}), \quad (4)$$

$$z_i = \exp\left[-\frac{1}{2\sigma^2}\sum_{j=1}^{P} w_{ij}^2(x_{kj}-m_{ji})^2\right], \quad (5)$$

$$u_i = z_i \Big/ \sum_{j=1}^{c} z_j. \quad (6)$$

In the above equations, σ is a real constant greater than zero, which represents the "fuzziness" of the classification. Other variables in these equations are described below and in the drawings.

In feature-weighted detector (FWD) networks, to select features, there are two types of learning when input is presented to the input layer. They are memory learning and weight learning. $m_i$ represents the memory learning result of neuron i. Memory learning is therefore unsupervised, and the change in $m_i$ in the learning process may be written as $\Delta m_i = \alpha_t u_i(x_k)(x_k - m_i)$, where $x_k$ represents the k-th input. On the other hand, weight connection $w_{ij}$ represents the degree to which feature j contributes to cluster i. In order to find the degree of importance of each feature to each cluster, the following error function is introduced $$E = \frac{1}{2}\sum_{k=1}^{N}\sum_{i=1}^{c}(u_i(x_k)-d_i)^2, \quad (7)$$

where $d_i$ is the desired value of output layer node i. Based on the chain rule of differential calculus, using Eqs. (7), (6) and (5) the following updating rule is obtained:

$$\Delta w_{ij} = \frac{\beta}{\sigma^2 s^2}(u_i(x_k)-d_i)(s-z_i)w_{ij}z_i(x_{kj}-m_{ji})^2, \quad (8)$$

where $$s = \sum_{i=1}^{c} z_i$$

and β>0 is learning rate. For the sake of understanding easily, $0 \leq w_{ij} \leq 1$ for each i and j. $w_{ij}=0$ means that feature j makes no contribution to cluster i; and $w_{ij}=1$ means that feature j makes the greatest possible contribution to cluster i. The corresponding algorithm is stated as follows:

1. Fix σ>0, α∈[0, 1], β>0, ε>0, and the maximum number of iterations T.
2. Initialize $\{m_i(0)\}$, using c samples randomly chosen from $\{x_k\}$ (k=1, . . . , N), and $w_{ij}(0)=1$ for each i and j.
3. For t=1, 2, . . . , T, For k=1, 2, . . . , N
   a. Calculate $\{u_i\}$ using Eq. (6).
   b. Update $\{m_i(t)\}$ using $\Delta m_i = \alpha_t u_i(x_k)(x_k - m_i)$
   c. Update $\{w_{ij}(t)\}$ using Eq. (8).
   d. Next k.
4. Calculate E using Eq. (7).
5. IF E<ε, or t>T stop, ELSE next t.

Outputs of the feature selection part 4200 include position of suspect nodules and their selected features (4205).

Figure 8:
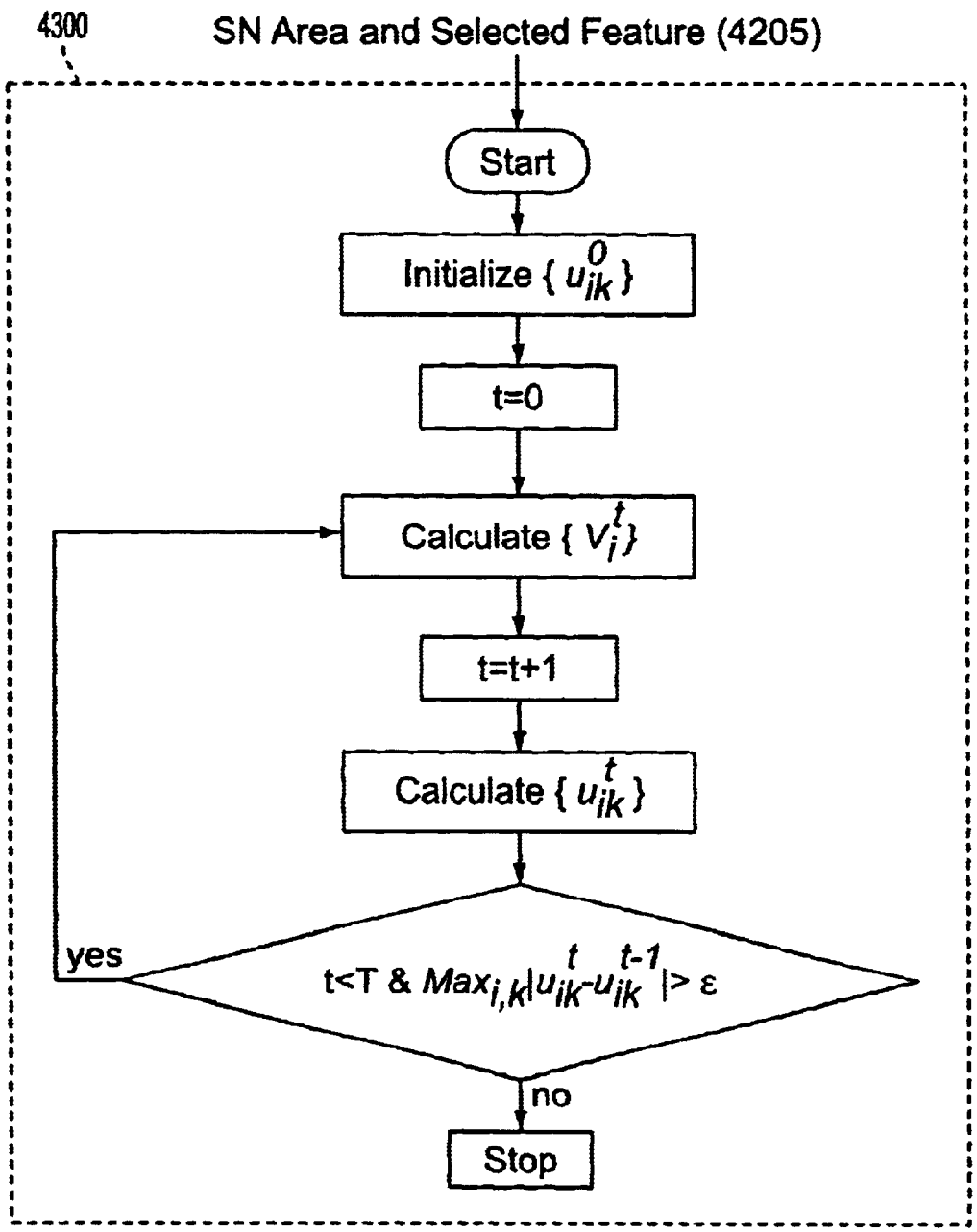
FIG. 8 is a flow chart illustrating steps in the nodule pre-grouping part of the classification unit of FIG. 4.

In the suspect nodules pre-grouping part 4300, a fuzzy clustering algorithm is employed. FIG. 8 is a flow chart depicting the method. In FIG. 8, $$u_{ik} = \exp[-\|x_k - v_i\|^2/2\sigma^2] \Big/ \sum_{j=1}^{c} \exp[-\|x_k - v_j\|^2/2\sigma^2],$$

and $$v_i = \sum_{k=1}^{N} u_{ik}x_k \Big/ \sum_{k=1}^{N} u_{ik}.$$

After clustering, the center of each cluster and the corresponding membership function are determined as described in Li, R. P. and Mukaidono, M., "Gaussian clustering method based on maximum-fuzzy entropy interpretation", *Journal of Fuzzy Sets and Systems*, 102 (1999), pp. 253–258, which is incorporated herein by reference.

Figure 4:
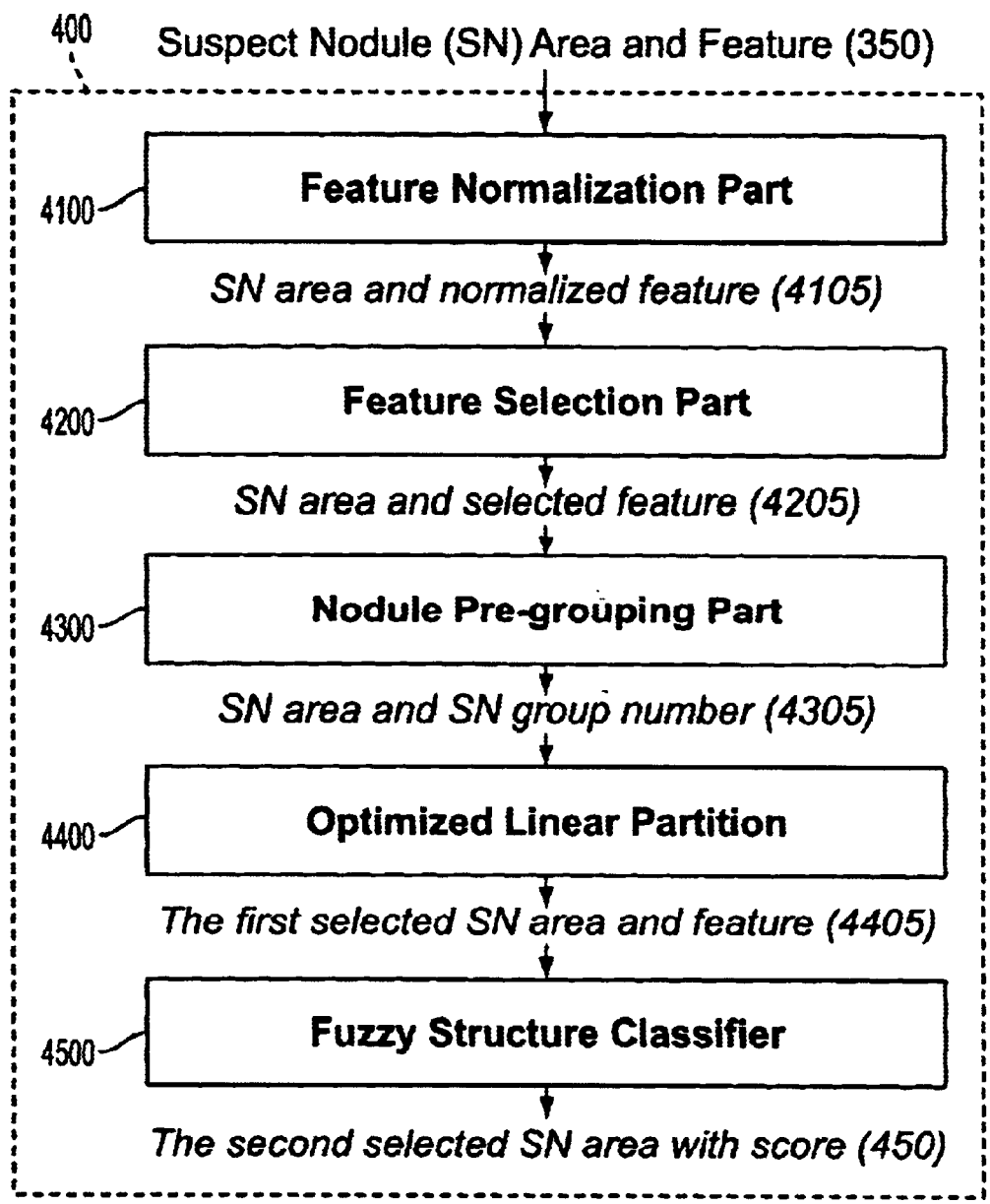
FIG. 4 is a block diagram of a classification unit of the detection unit of FIG. 3.

The optimized linear partition (OLP) part 4400 of FIG. 4 serves as the first level classifier as well as a sample reduction method to reduce number of training samples for further detailed and comprehensive training. The aim is to remove those false positive nodules whose features do not overlap with features of true positive nodules. Usually, those non-overlapping false positive nodules constitute the majority of the suspect nodules. According to the method of the present invention, this optimal linear partition was derived from the problem:

$$\underset{(w_{ij})}{\text{Minimize}}\left\{\sum_{k=1}^{k=N}(t_k - y_k)^2\right\}.$$

Here, $y_k$ and $t_k$ represent the k-th actual output and desired output corresponding to input vector $x_k$, respectively; $y_k = f(x_k)$ is a linear function of x; and N is the number of patterns to be used for training. The algorithm is as follows:

1. For k=1, 2, . . . , N, where $x_k=(x_{k1}, x_{k2}, \ldots, x_{kM})$, N represents the number of patterns (suspect nodules) presented to the classifier, and M represents the number of features.
2. For i=1, 2, . . . P, P representing the number of linear partitions, where one-linear partition corresponds to one classifier:
   a) Calculate $y_k = w_i \cdot x_k^T$, where $w_i$ represents the coefficient vector of the i-th classifier obtained by using equation $$\underset{(w_{ij})}{\text{Minimize}}\left\{\sum_{k=1}^{k=N}(t_k - y_k)^2\right\}.$$

b) IF $y_k < \theta_i$, THEN $x_k$ is a false positive nodule. Otherwise, $x_k$ remains as a suspect nodule candidate to present to the next classifier. Here, $\theta_i$ is the threshold of the i-th classifier.
   c) If i<P, next i.
3. If k>N, output remaining suspect nodule candidates-to next step. Otherwise, next k.

Figure 9:
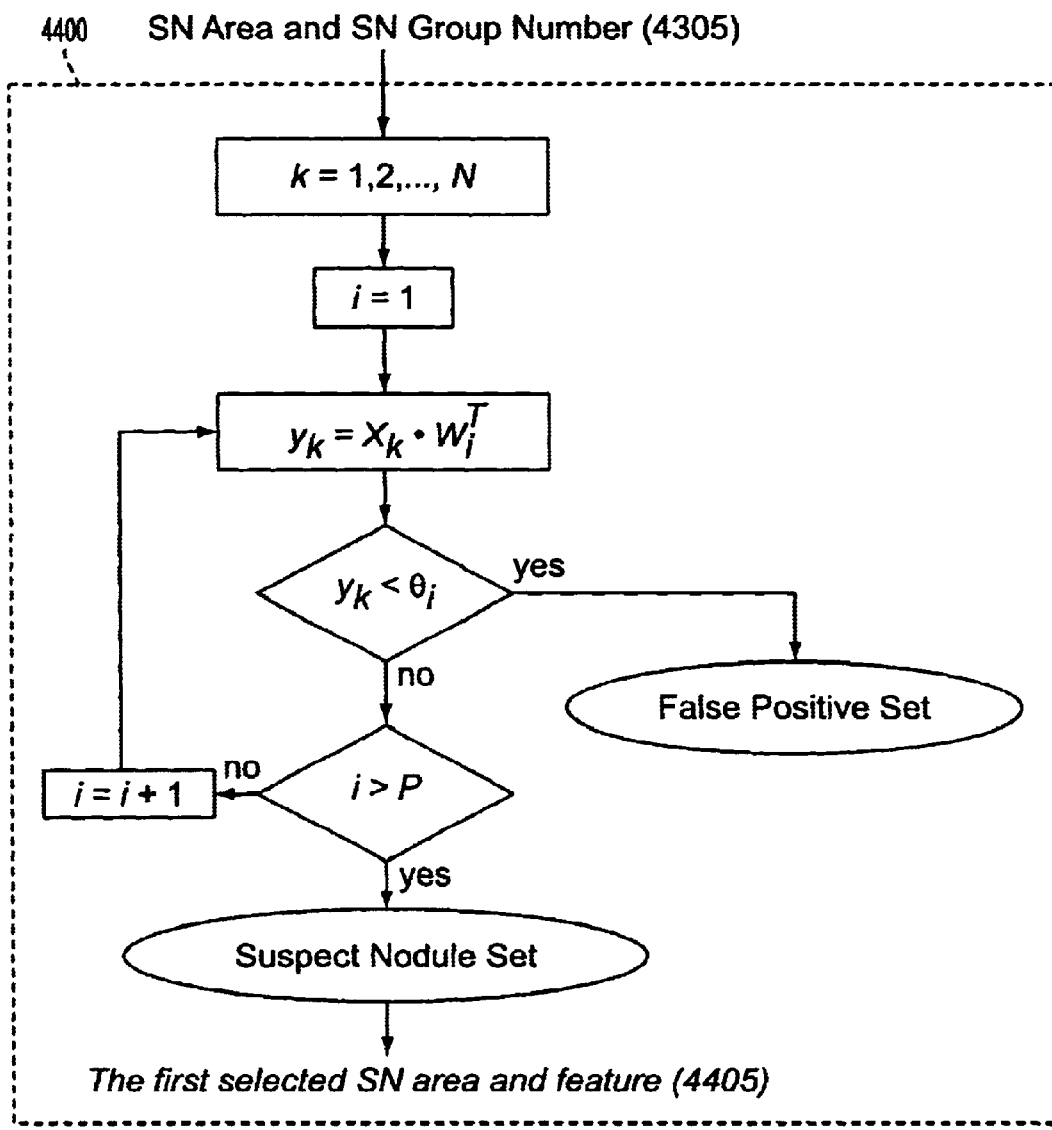
FIG. 9 is a flow chart illustrating steps in the OLP part of the classification unit of FIG. 4.

The flow chart of the algorithm is shown in FIG. 9. Outputs of the optimized linear partition part are position of the first selected SNs and their features (4405).

The fuzzy structure classifier part 4500 is the second level classifier based on a semi-supervised learning scheme. The aim is further to reduce those false positive nodules that overlap with true positive nodules. According to the method of the invention, a fuzzy structure classifier consists of a set of rules that are of IF-THEN form. The premise part of each rule expresses fuzzy structures in data. The consequence part of each rule expresses a clear relationship between inputs and output. Therefore, each rule can be described in natural language. Rule $\Re$ is of the following form: IF $x_1$ is $m_{i1}$ and $x_2$ is $m_{i2}$ . . . and $x_p$ is $m_{ip}$, THEN $$o_i = \sum_{n=1}^{p} w_{in} x_n^{d_{in}} + w_{i0}.$$

Here, $\Re$ (i=1, 2, . . . , c) denotes the i-th rule, $x=(x_1, x_2, \ldots, x_p) \in R^p$ represents a p-dimensional input vector, $o_i$ is output of the rule $\Re$, and $m_{ij}$ represents a fuzzy set of the input space. For each i and j, $w_{ij} \in R$ and $d_{ij} \in R$. The present model is almost structure-free. When $d_{ij}=0$ for each i and j, the THEN part of rule becomes a constant; thus a hyper-ball-like data structure is described by the model. When $d_{ij}=1$ for each i and j, the THEN part of rule becomes a linear function; thus a hyper-plane-like data structure is described by the model. When input $x_k$ is presented to the classifier, the final output is calculated by defuzzification as follows:

$$y'_k = \sum_{i=1}^{c} u_{ik} o_i \bigg/ \sum_{i=1}^{c} u_{ik},$$

where $$u_{ik} = \prod_{j=1}^{p} m_{ij}(x_{kj}).$$

Figure 10:
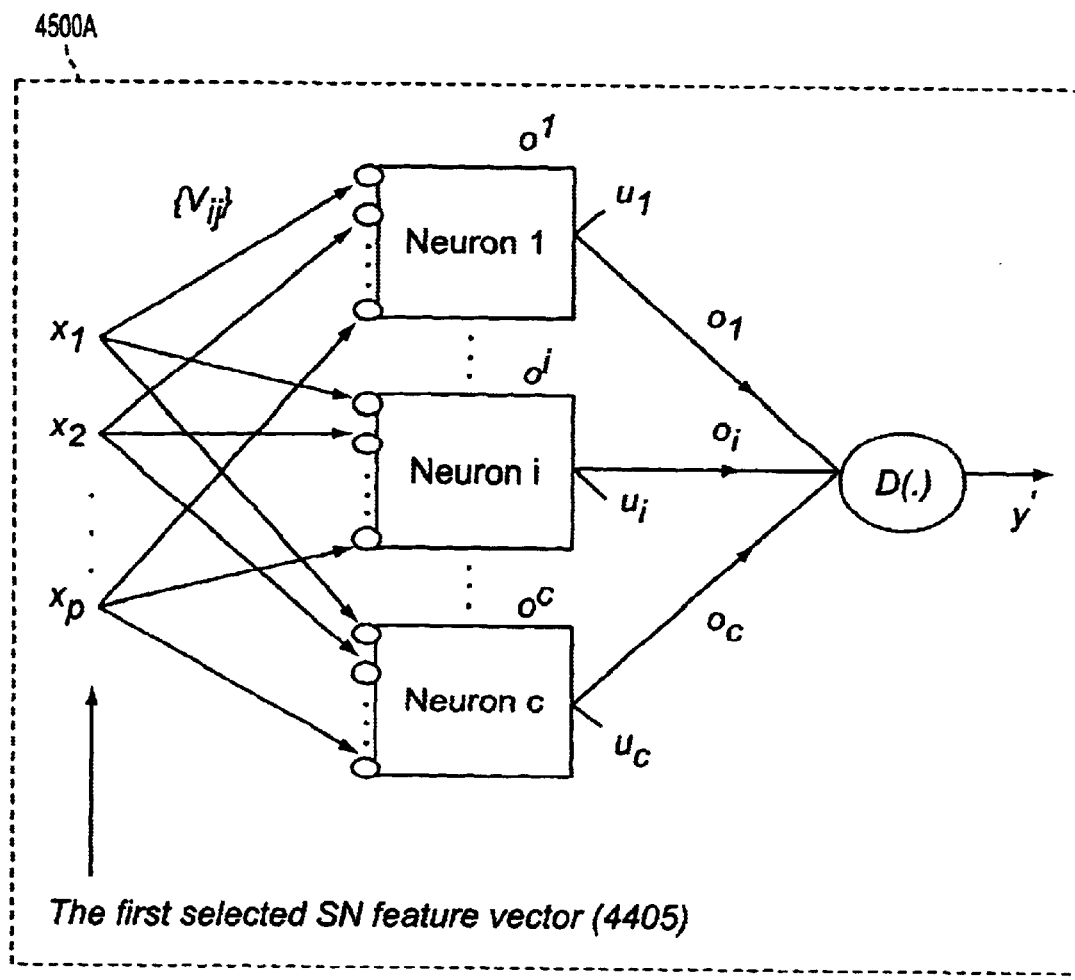
FIG. 10 is a schematic diagram of the FSC network in the FSC part of the classification unit of FIG. 4.
Figure 11:
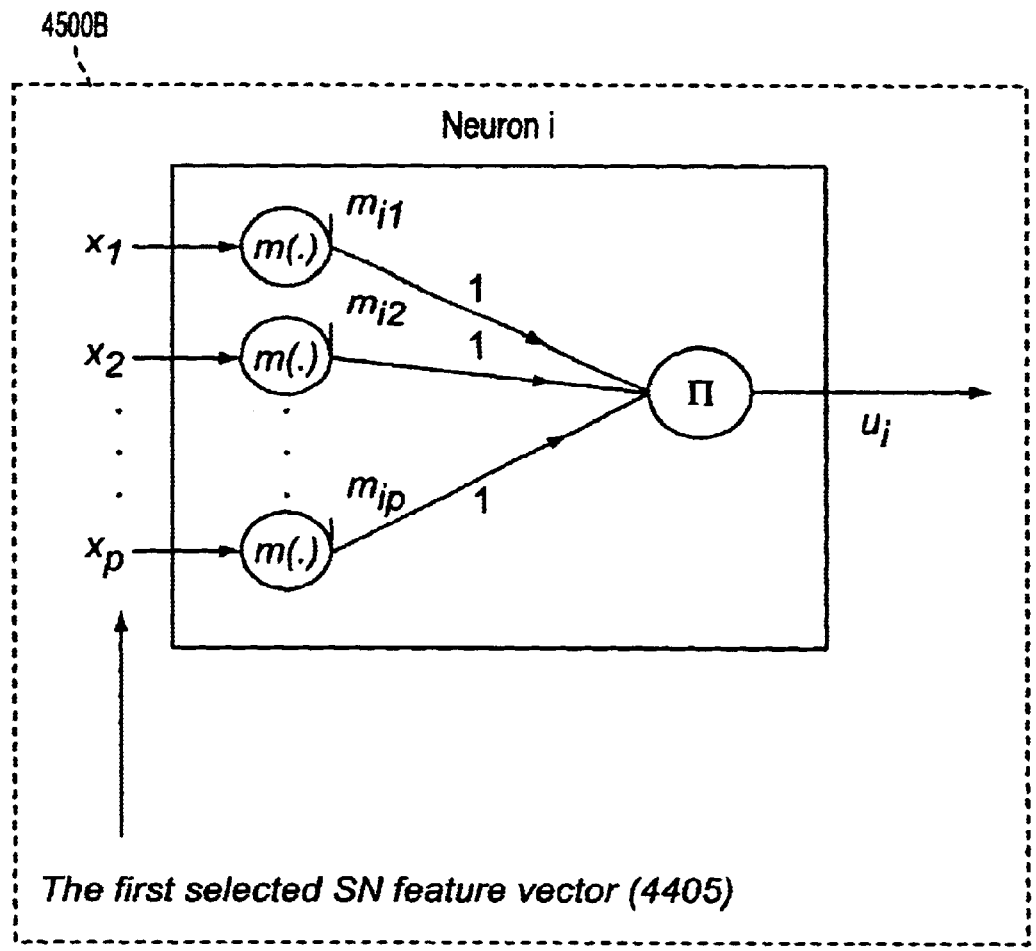
FIG. 11 is the structure of hidden neuron i in the FSC part of the classification unit of FIG. 4.

FIGS. 10 and 11 depict a schematic diagram of the fuzzy structure classifier (FSC) network. The identification of a fuzzy structure classifier includes two parts: structure identification and parameter identification. The purpose of structure identification is to find the optimal number of rules. According the method of the invention, a fuzzy clustering algorithm is employed to find the optimal number of rules. The algorithm used is described in Li, R. P. and Mukaidono, M., "Fuzzy modelling and clustering neural network", *Journal of Control and Cybernetics*, 25 (1996), pp. 225–242, which is incorporated herein by reference.

On the other hand, parameter identification is based on the network of FIG. 10. A fuzzy structure classifier network consists of three layers. The number of input layer neurons is equal to the number of features selected by the feature selection part 4200. The number of hidden layer neurons is equal to the number of rules determined by the above structure identification. There is a single output. The parameter updating rules are the following:

1. $\Delta d_{ij} = \eta g w_{ij} x_{kj}^{d_{ij}} \log(x_{kj})$;
2. $\Delta w_{ij} = \eta g x_{kj}^{d_{ij}}$;
3. If $x_{kj} \leq v_{ij}$, then
   $\Delta v_{ij} = \eta g (o_i - y'_k)(x_{kj} - v_{ij})/(\sigma_{jl}^i)^2$,
   $\Delta \sigma_{jl}^i = \eta g (o_i - y'_k)(x_{kj} - v_{ij})/(\sigma_{jl}^i)^3$;
4. If $x_{kj} \geq v_{ij}$, then
   $\Delta v_{ij} = \eta g (o_i - y'_k)(x_{kj} - v_{ij})/(\sigma_{jr}^i)^2$,
   $\Delta \sigma_{jr}^i = \eta g (o_i - y'_k)(x_{kj} - v_{ij})/(\sigma_{jr}^i)^3$.

Here, $$g = (y_k - y'_k) u_{ik} \bigg/ \sum_{i=1}^{c} u_{ik},$$

and $\eta$ is the learning rate. The processing procedure of the FSC is as follows:

STEP 1: Identify the structure of the FSC, i.e., to find the optimal number of rules.

STEP 2: Identify the parameters of the FSC using the above updating rules.

Figure 12:
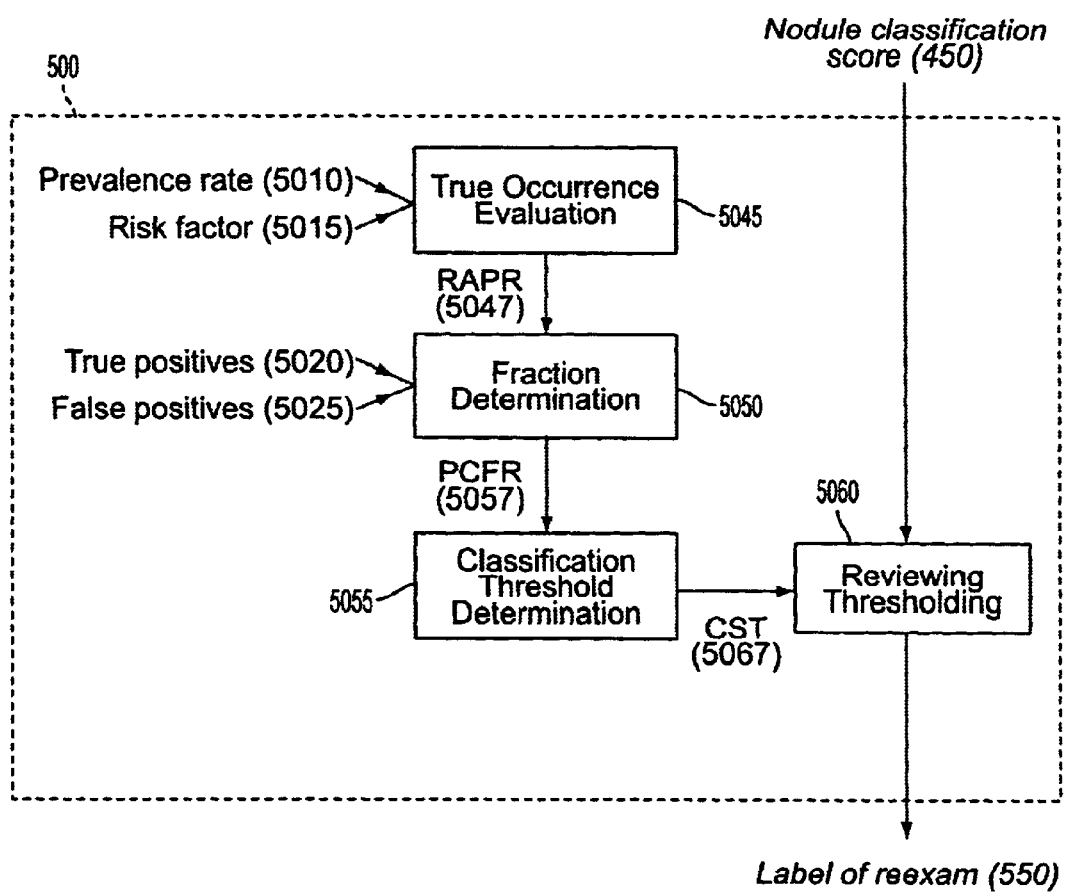
FIG. 12 is a block diagram of a decision-making unit forming part of the detection unit of FIG. 3.

FIG. 12 illustrates a decision making unit 500 in FIG. 3 to select a certain percentage of cases for further review by a physician or by another device based on the nodule classification score 450. The disease prevalence rate 5010 and risk factor 5015 are first fed into the true occurrence evaluation unit 5045 to determine the risk-adjusted prevalence rate, RAPR 5047 (frequency of the disease for population with risk factor 5015). For lung nodule detection, the prevalence rate 5010 in the U.S. was around 160,000 in 1996, and the risk factor for a high-risk population was around 10 times that of the general population. Both prevalence rate and high-risk factor change each year and among different populations. The RAPR 5047 from unit 5045 and the performance of the detection system (including number of true positives 5020 and number of false positives 5025) are fed into the fraction determination unit 5050 in order to obtain the percentage of the cases for further review, PCFR 5057. The PCFR 5057 is obtained by performing the summation of false positives and risk-adjusted prevalence rate 5047. The PCFR 5057 is then fed into the classification score determination unit 5055 to determine the classification score thresholds, CST 5067 (such as circularity, neural network score, etc.). In reviewing thresholding unit 5060, the nodule classification score 450 is further evaluated by comparing the classification score with classification score threshold, CST 5067. Those satisfying the CST 5067 are marked with the label for re-exam 550 and will be sent for further diagnostic review.

It should be understood that the methods and systems described herein may be modified within the scope of the invention. For example, while the inventive methods and systems are described herein in connection with the detection of lung nodules, it should be clear that these methods and systems may be used for detecting other types of cancer such as microcalcification clusters or masses in breast cancer, nodules, lumps, irregularities, or tumors in other body parts. Furthermore, although the current invention uses chest x-ray images as examples, it is clear that this invention can be used in other imaging modalities such as CT, MRI, mammography, and ultrasound images. The current inventive methods and systems may also be modified for other pattern recognition problems such as non-destructive defect detection in chip sets and automobile industry, earth surface classification, identification of friendly or enemy targets (aircraft, tanks, etc.), and so on.

What is claimed is:

1. A fuzzy logic based classification (FLBC) method for discriminating abnormal objects from normal objects based on their features, the method comprising the steps of:
    a) normalizing features of said objects;
    b) selecting important features from among the normalized features;
    c) pre-grouping said objects based on the selected features and labeling each of said objects with a group number;
    d) subjecting said objects to trained linear classifiers corresponding to their group numbers to identify suspected abnormal objects; and e) subjecting said suspected abnormal objects that pass said linear classifier to a trained fuzzy classifier for further discriminating between abnormal and normal objects.

2. The method of claim 1, wherein said normalizing step comprises:

performing vertical offset normalization of said features; and outputting the values of the resulting normalized features for each of said objects.

3. The method of claim 2, said vertical offset normalization step includes the step of removing a mean value.

4. The method of claim 1, wherein said step of selecting important features comprises the steps of:

performing feature selection on said normalized features; and assigning a degree of importance of each feature based on known target data.

5. The method of claim 4, said feature selection step comprising the steps of:

performing data analysis to obtained analyzed data;

passing said analyzed data through at least one neural network means, said at least one neural network means including at least one fuzzy neural network means and fuzzy clustering means.

6. The method of claim 5, said step of passing the analyzed data through at least one neural network means including the steps of:

passing said analyzed data through a feature-weighted detector (FWD) having weight connections for evaluating degree of importance of feature and memory connections for classifying patterns; and outputting selected features, whose weight is greater than a threshold.

7. The method of claim 6, wherein at least one of said at least one neural network comprises: a three layer and feed-back neural network having gaussian functions for hidden neurons; an unsupervised learning rule for said weight connections; and a supervised learning rule for said memory connections.

8. The method of claim 6 in which said weight connections are forward-connections between input layer and hidden layer and said memory connections are feedback-connections between hidden layer and input layer.

9. The method of claim 1, said step of pre-grouping comprises using unsupervised learning schemes and supervised schemes to classify said objects.

10. The method of claim 9, further including the step of using fuzzy clustering methods to classify said objects based on said unsupervised learning scheme.

11. The method of claim 10, said step of using fuzzy clustering methods including the step of using a gaussian clustering method having inputs comprising said selected features and output including a group number that belongs to a corresponding one of said objects.

12. The method of claim 1, wherein said step of subjecting said objects to trained linear classifiers comprises the steps of:

using optimization means; and using neural network means.

13. The method of claim 12, in which said step of using optimization means further includes the steps of:

performing optimized linear partitioning (OLP) that corresponds to a solution of a problem of optimization of an unconstrained quadratic function;

using said suspect objects that have said selected features;

determining thresholds;

eliminating false abnormal objects; and outputting first selected abnormal objects.

14. The method of claim 13 in which said problem of optimization of unconstrained quadratic function is $$\underset{\{w_{ij}\}}{Minimize}\left\{\sum_{k=1}^{k=N}(t_k-y_k)^2\right\},$$

where $y_k$ and $t_k$ represent the k-th actual output and desired output corresponding to an input vector $x_k$, respectively; $y_k=f(x_k)$ is a linear function of x; N is a number of patterns to be used for training; and $\{w_{ij}\}$ are weights used in computing $y_k=f(x_k)$.

15. The method of claim 1, wherein said step of subjecting said suspected abnormal objects to a trained fuzzy classifier includes the steps of:

using a fuzzy structure classifier (FSC) network to remove false abnormal objects that are not separable linearly using the pre-grouped abnormal objects as inputs;

determining a threshold;

calculating a score for each of said suspected abnormal objects not eliminated using said FSC network;

eliminating further false abnormal objects based on their scores; and outputting the remaining suspected abnormal objects and their corresponding scores.

16. The method of claim 1, wherein step e) includes the step of determining a classification score for each of said suspected abnormal objects.

17. The method of claim 16, further comprising the step of:

f) deciding, based on said classification scores, which of said suspected abnormal objects will be labeled for further diagnostic review.

18. The method of claim 17, wherein the step of deciding further comprises the steps of:

determining a risk adjusted prevalence rate (RAPR), based on a prevalence rate and a risk factor;

determining a percentage of cases for further review (PCFR), based on said RAPR;

determining a classification threshold based on said PCFR; and using said classification threshold to determine, based on said classification scores, which of said suspected abnormal objects will be labeled for further diagnostic review.

19. A computer-readable medium containing software implementing the method of claim 1.

20. A system that performs fuzzy logic based classification for discriminating abnormal objects from normal objects based on their features, the system comprising:

a computer system; and a computer-readable medium containing software implementing the method of claim 1.

21. A fuzzy logic based classification system for discriminating abnormal objects from normal objects based on their features, the system comprising:

means for normalizing features of said objects;

means for selecting important features from among the normalized features of said objects;

means for pre-grouping of objects according to their selected features and for labeling each of said objects with a corresponding group number;

means for performing optimized linear partitioning to identify suspected abnormal objects; and a fuzzy structure classifier for further discriminating suspected abnormal objects and assigning a classification score to each of said suspected abnormal objects.

22. The fuzzy logic based classification system of claim 21, further comprising means for selecting suspected abnormal objects for further diagnostic review based on said classification scores.

23. The fuzzy logic based classification system of claim 22, wherein said means for selecting suspected abnormal objects comprises:

means for determining a risk adjusted prevalence rate (RAPR) based on a prevalence rate and a risk factor;

means for determining a percentage of cases for further review (PCFR) based on said RAPR;

means for determining a classification threshold based on said PCFR; and means for comparing each of said classification scores with said classification threshold to determine which of said suspected abnormal objects will be labeled for further diagnostic review.

24. The fuzzy logic based classification system of claim 21, said means for normalizing comprising vertical offset normalization means, said vertical offset normalization means removing a mean value.

25. The fuzzy logic based classification system of claim 21, said means for selecting important features comprising:

data analysis means;
at least one neural network;
at least one fuzzy neural network; and
fuzzy clustering means.

26. The fuzzy logic based classification system of claim 25, wherein said fuzzy neural network including a feature-weighted detector having weight connections for evaluating degrees of importance of features and memory connections for classifying patterns.

27. The fuzzy logic based classification system of claim 26, said fuzzy neural network further comprising:

a three-layer feedback neural network having gaussian functions for hidden neurons, said three layers being an input layer, a hidden layer, and an output layer;

wherein an unsupervised learning rule is used for said weight connections and a supervised learning rule is used for said memory connections.

28. The fuzzy logic based classification system of claim 27, wherein said weight connections are forward connections between said input layer and said hidden layer, and wherein said memory connections are feedback connections between said hidden layer and said input layer.

29. The fuzzy logic based classification system of claim 21, said means for pre-grouping utilizing unsupervised learning schemes and supervised learning schemes to classify said objects.

30. The fuzzy logic based classification system of claim 29, said means for pre-grouping including means for fuzzy clustering to classify said objects based on an unsupervised learning scheme.

31. The fuzzy logic based classification system of claim 30, wherein said means for fuzzy clustering includes means for performing a gaussian clustering operation in which selected features are input and a corresponding group number is assigned to the object associated with the selected features.

32. The fuzzy logic based classification system of claim 21, said means for performing optimized linear partitioning comprising:

optimization means; and
neural network means.

33. The fuzzy logic based classification system of claim 32, said optimization means implementing an optimized linear partition corresponding to a solution of an unconstrained quadratic optimization problem.

34. The fuzzy logic based classification system of claim 33, wherein said unconstrained quadratic optimization problem is $$\underset{\{w_{ij}\}}{Minimize}\left\{\sum_{k=1}^{k=N}(t_k-y_k)^2\right\},$$

where $y_k$ and $t_k$ represent the k-th actual output and desired output corresponding to an input vector $x_k$, respectively; $y_k=f(x_k)$ is a linear function of x; N is a number of patterns to be used for training; and $\{w_{ij}\}$ are weights used in computing $y_k=f(x_k)$.

35. The fuzzy logic based classification system of claim 21, said means for performing optimized linear partitioning comprising a fuzzy structure classifier network that removes false abnormal objects that are not linearly separable, using the pre-grouped objects as inputs; calculates classification scores for said objects; further discriminating among the objects based on said classification scores; and outputting the resulting objects and their corresponding classification scores as suspected abnormal objects.

36. A method of discriminating different objects in an image, comprising the steps of:

applying optimal linear partitioning to the image, the step of applying optimal linear partitioning comprising the step of performing optimization on a set of suspected target objects; and applying neural network means to outputs of the step of performing optimization, wherein the step of performing optimization further includes the steps of:

performing optimized linear partitioning (OLP) that corresponds to a solution of a problem of optimization of an unconstrained quadratic function;

using features of objects;
determining thresholds;
eliminating false target objects; and
outputting first selected target objects.

37. The method of claim 36 in which said problem of optimization of an unconstrained quadratic function is $$\underset{\{w_{ij}\}}{Minimize}\left\{\sum_{k=1}^{k=N}(t_k-y_k)^2\right\},$$

where $y_k$ and $t_k$ represent the k-th actual output and desired output corresponding to an input vector $x_k$, respectively; $y_k=f(x_k)$ is a linear function of x; N is a number of patterns to be used for training; and $\{w_{ij}\}$ are weights used in computing $y_k=f(x_k)$.

* * * * *